United States Patent [19]

Sarbach

[11] 3,950,531
[45] Apr. 13, 1976

[54] MEDICINE COMPRISING THE BENZILIC ESTER OF (DIMETHYL-2',5' PYRROLIDINO)-2-ETHANOL

[75] Inventor: Raymond François Sarbach, Chatillon-sur-Chalaronne, France

[73] Assignee: Institut de Recherche Scientifique I.R.S., Chatillon-sur-Charlaronne, France

[22] Filed: Mar. 27, 1973

[21] Appl. No.: 345,480

[30] Foreign Application Priority Data
Apr. 28, 1972 France ............................. 72.10862

[52] U.S. Cl. ................................................ 424/274

[51] Int. Cl.$^2$......................................... A61K 31/40
[58] Field of Search .................................... 424/274

[56] References Cited
OTHER PUBLICATIONS
Chemical Abstracts 57:16544e–16545f (1962).

Primary Examiner—Jerome D. Goldberg
Attorney, Agent, or Firm—Browdy and Neimark

[57] ABSTRACT

The medicine is composed of the benzilic ester of (dimethyl-2', 5'-pyrrolidino)-2-ethanol and the N-methyl bromide thereof. The medicine is used for treating ulcers and spasms.

13 Claims, No Drawings

MEDICINE COMPRISING THE BENZILIC ESTER OF (DIMETHYL-2',5' PYRROLIDINO)-2-ETHANOL

The present invention relates to the introduction in human and veterinary therapeutics of a benzilic ester of the (dimethyl-2', 5'-pyrrolidino)-2-ethanol having a very noticeable anti-ulcerous effect and a very important spasmolytic activity.

The present invention particularly uses the N-methyl bromide of the benzilic ester of (dimethyl-2', 5'-pyrrolidino)-2-ethanol.

The benzilic ester of (dimethyl-2', 5'-pyrrolidono)-2-ethanol is a new compound and is prepared by condensing the chloro-amine obtained from the preceding amino-alcohol on the benzilic acid in isopropanol, according to the usual method of HORENSTEIN and PAHLICKE (Ber-1938, 71 B, 1654).

According to the invention, the anti-ulcerous and spasmolytic medicine comprises the benzilic ester of (dimethyl-2',5'-pyrrolidino)-2-ethanol, prepared by condensation of chloroamine obtained from the preceding amino-alcohol on benzilic acid in isopropanol.

Benzilic ester of (dimethyl-2',5' pyrrolidino)-2-ethanol

Preparation

The compound is prepared by: introducing in a flask, having a capacity of 250 ml provided with a mechanical stirrer and a cooling device, 22.8 g (0.10 mole) of benzilic acid, 16.2 g (0.10 mole) of (dimethyl-2', 5' pyrrolidino)-2 chloro-1 ethane and 60 ml of isopropanol; heating at reflux during 12 hours; dry-evaporating in a water-bath under vacuum; stirring; the obtained residue with 250 ml of water; alkalinizing with soda carbonate(aqueous solution at 10%); extracting with ether, then washing the ethereal solution with water; drying on anhydrous soda sulfate and lastly evaporating the solvent and then distilling.

Obtained amount: 22.6 g
Yield: 64%

Properties:
Light yellow sticky oil, $BP_{0.1} = 185° - 187°C$.
IR spectrum
2.84 (OH), 3.25

3.37 ($CH_2$, $CH_3$) 5.80 (C=O) 8.10 $\mu$ (C — O — C).

N-methyl bromide of the benzilic ester of (dimethyl-2', 5' pyrrolidino)-2-ethanol Preparation The compound is prepared by: letting in contact at room temperature during one night 3.53 g (0.01 mole) of benzilic ester dissolved in 25 ml of acetone with 5 ml of methyl bromide; drying the crystals so formed; washing them with acetone and then drying at 55°C under reduced pressure.

Obtained amount: 4.2 g
Yield: 95%

Properties

Colorless crystals, MP = 183° – 184°C (after recrystallization in ethanol at 95% - ethyl acetate, the product melts at 186°C – 187°C); soluble in water and in alcohol, little solubility in acetone, ether, ethyl acetate.

Analysis: $C_{23}H_{30}$ Br N $O_3$ = 448

|  | C | H | N |
|---|---|---|---|
| Calculated % | 61.65 | 6.69 | 3.12 |
| Found | 61.40 | 6.69 | 3.24 |

Pharmacology elements for the N-methyl bromide of the benzilic ester of (dimethyl-2', 5' -pyrrolidino)-2-ethanol Acute toxicity The $LD_{50}$ has been determined for the mouse SWISS by two methods of administration: intra-peritoneal method and oral method.

Results:
I.P. method $LD_{50}$ = 125 mg/Kg
Oral method $LD_{50}$ = 1120 mg/Kg

Spasmolytic activity

Tested on the isolated duodenum of rat.

Neurotrope field: the contraction caused by 0.4 $\mu$g of acetylcholine is inhibited by 50% through addition of:
0.4 $\mu$g of N-methyl bromide of the benzilic ester of (dimethyl-2', 5' pyrrolidino)- 2-ethanol,
or through 2 $\mu$g of N-butyl-hyoscine bromide (Buscopan),
or through 2 $\mu$g of thiemonium (Visceralgine).

Muscolotrope field: the contraction caused by 2 mg of barium chloride is inhibited by 50% through addition of:
2 to 2.5 $\mu$g of N-methyl bromide of the benzilic ester of (diemethyl-2',5' pyrrolidino)-2-ethanol,
or 20 to 25 mg of N-butyl-hyoscine bromide,
or 150 $\mu$g of papaverine chlorhydrate.

Besides the cholinolytic activity of the N-methyl bromide of the benzilic ester of (dimethyl-2',5' pyrrolidino)-2-ethanol has been compared to the activity of atropine in rats. The effect has been measured in vivo on the carotid pressure and on the intestinal motivity.

The average results (obtained each time on lots of five rats) are as follows:

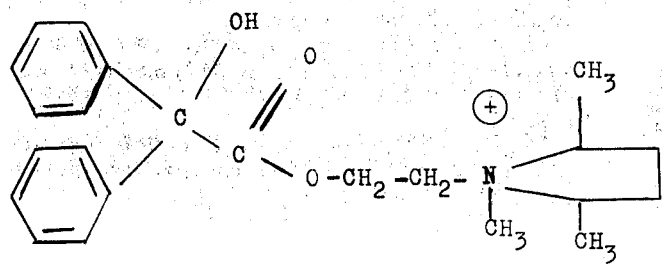

| ATROPIN (sulphate) | Time after injection | Tensional effect | Intestinal motivity |
|---|---|---|---|
| 1 mg/kg I.V. method Cholinolytic effect after injection | 5 min | 43 % | 47 % |
| | 10 min | 42 % | 42 % |
| | 20 min | 41 % | 38 % |
| | 30 min | 39 % | 28 % |

N-methyl bromide of the benzilic ester of (dimethyl-2', 5'pyrrolidino)-2-ethanol

| | Time after injection | Tensional effect | Intestinal motivity |
|---|---|---|---|
| 1 mg/kg I.V. method Cholinolytic effect after injection | 5 min | 45 % | 36 % |
| | 10 min | 45 % | 36 % |
| | 20 min | 45 % | 36 % |
| | 30 min | 45 % | 36 % |

In such conditions the lowered blood pressure is of:
37% with atropine
25% with the N-methyl bromide of the benzilic ester of the (dimethyl-2', 5'-pyrrolidino)-2-ethanol.
In both cases, said low blood pressure remains no more than 2 or 3 minutes.

Anti-ulcerous activity

This study has been made on rats having reserpinic ulcers according to the following test.

Female rats of WISTAR stock, are placed in separate metallic cages, without any food and drink for 72 hours.

At times 24 h and 48 h, the rats are given by introperitoneal method, 0.5 mg/rat of reserpine (Serpasil injectable). At times 0, 24 and 48 h, the rats are given by oral method the N-methyl bromide of the benzilic ester of (dimethyl-2', 5' pyrrolidino) 2-ethanol in suspension in sticky water at 2%, the grade of the different suspensions is calculated in such a way that the animals are given 0.5 ml/100 g.

After 72 hours, the animals are killed, the stomachs taken out and it is noticed the eventual presence of ulcers, the seriousness of the same and their number by rat. All these readings are made blindly.

The animals which were used are:
Batch 1 - Standards (reserpine only)
Batch 2 - N-methyl bromide of the benzilic ester of (dimethyl-2',5'-pyrrolidino)-2-ethanol: 12.5 mg/kg;
Batch 3 - N-methyl bromide of the benzilic ester of (dimethyl-2,5'-pyrrolidino)-2-ethanol: 37.5 mg/kg.
Batch 4 - N-methyl bromide of the benzilic ester of the (dimethyl-2',5'-pyrrolidino)-2-ethanol: 50 mg/kg.

Results:

| | ULCERATIONS | | | Index of average ulcer |
|---|---|---|---|---|
| | Incidence % | Seriousness | Number per rat | |
| STANDARDS N-methyl | 100 % | 1.22 | 2.88 | 14.1 |
| bromide of the benzilic ester of (dimethyl-2',5'-pyrrolidino)-2-ethanol | | | | |
| 12.5 mg/kg | 86 % | 1.14 | 3.14 | 12.9 |
| 37.5 mg/kg | 71 % | 0.71 | 0.86 | 8.7 |
| 50 mg/kg | 43 | 0.43 | 1.28 | 6.0 |

I claim:
1. A method of treating stomach ulcerations in a human or veterinary patient in need of said treatment, comprising administering to said patient an effective anti-ulcerous amount of a compound selected from the group consisting of the benzilic ester of (dimethyl-2',-5'-pyrrolidino)-2-ethanol and a pharmaceutically acceptable salt thereof.
2. A method in accordance with claim 1 wherein said compound is the N-methyl bromide of the benzilic ester of (dimethyl-2',5'-pyrrolidino)-2-ethanol.
3. A method in accordance with claim 1 wherein said compound is the benzilic ester of (dimethyl-2',5'-pyrrolidino)-2-ethanol.
4. A method in accordance with claim 3 wherein said composition is administered in a dosage of 12.5 mg/kg to 50 mg/kg.
5. A method in accordance with claim 1 wherein said composition is administered in a dosage of 12.5 mg/kg to 50 mg/kg.
6. A method of treating spasms in a human or veterinary patient in need of said treatment, comprising administering to said patient an effective spasmolytic amount of a compound selected from the group consisting of the benzilic ester of (dimethyl-2',5'-pyrrolidino)-2-ethanol and a pharmaceutically acceptable salt thereof.
7. A method in accordance with claim 6 wherein said compound is the N-methyl bromide of the benzilic ester of (dimethyl-2',5'-pyrrolidino)-2-ethanol.
8. A method in accordance with claim 7 wherein said composition is administered in a dosage of 12.5 mg/kg to 50 mg/kg.
9. A method in accordance with claim 6 wherein said compound is the benzilic ester of (dimethyl-2',5'-pyrrolidino)-2-ethanol.
10. A method in accordance with claim 6 wherein said composition is administered in a dosage of 12.5 mg/kg to 50 mg/kg.
11. An anti-ulcerous and spasmolytic composition comprisng the benzilic ester of (dimethyl-2',5'-pyrrolidino)-2-ethanol or a pharmaceutically acceptable salt thereof, as active ingredient, in an effective antiulcerous or effective spasmolytic amount, and a pharmaceutically acceptable excipient.
12. A composition in accordance with claim 11, wherein said active ingredient is the N-methyl bromide of the benzilic ester of (dimethyl-2',5'-pyrrolidino)-2-ethanol.
13. A composition in accordance with claim 11, wherein said active ingredient is the benzilic ester of (dimethyl-2',5'-pyrrolidino)-2-ethanol.

* * * * *

UNITED STATES PATENT OFFICE
CERTIFICATE OF CORRECTION

Patent No. 3,950,531　　　　　　　　Dated April 13, 1976

Inventor(s) Raymond Francois SARBACH

It is certified that error appears in the above-identified patent and that said Letters Patent are hereby corrected as shown below:

Item [30] Foreign Application Priority Data should read:
--March 28, 1972, France ...............72.10862--.

Signed and Sealed this

Twenty-fourth Day of August 1976

[SEAL]

Attest:

RUTH C. MASON
*Attesting Officer*

C. MARSHALL DANN
*Commissioner of Patents and Trademarks*